United States Patent
Matsuda et al.

(10) Patent No.: US 12,239,620 B2
(45) Date of Patent: Mar. 4, 2025

(54) METHODS TO DECREASE TRIGLYCERIDE SYNTHESIS IN THE LIVER

(71) Applicant: MediciNova, Inc., La Jolla, CA (US)

(72) Inventors: Kazuko Matsuda, La Jolla, CA (US); Masatsune Ogura, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 355 days.

(21) Appl. No.: 17/825,773

(22) Filed: May 26, 2022

(65) Prior Publication Data

US 2022/0387364 A1     Dec. 8, 2022

Related U.S. Application Data

(60) Provisional application No. 63/194,829, filed on May 28, 2021.

(51) Int. Cl.
*A61K 31/192* (2006.01)
*A61K 9/00* (2006.01)
*A61P 3/06* (2006.01)

(52) U.S. Cl.
CPC .......... *A61K 31/192* (2013.01); *A61K 9/0053* (2013.01); *A61P 3/06* (2018.01)

(58) Field of Classification Search
CPC .. A61K 31/015; A61K 31/192; A61K 9/0053; A61P 3/06; A61P 3/08
See application file for complete search history.

(56) References Cited

U.S. PATENT DOCUMENTS

| | | |
|---|---|---|
| 4,788,055 A | 11/1988 | Fischer et al. |
| 4,816,264 A | 3/1989 | Phillips et al. |
| 4,828,836 A | 5/1989 | Elger et al. |
| 4,834,965 A | 5/1989 | Martani et al. |
| 4,834,985 A | 5/1989 | Elger et al. |
| 4,985,585 A | 1/1991 | Ohashi et al. |
| 4,996,047 A | 2/1991 | Kelleher et al. |
| 5,071,646 A | 12/1991 | Malkowska et al. |
| 5,133,974 A | 7/1992 | Paradissis et al. |

(Continued)

FOREIGN PATENT DOCUMENTS

| | | |
|---|---|---|
| WO | WO 2015/013395 A1 | 1/2015 |
| WO | WO 2015/105874 A1 | 7/2015 |
| WO | WO 2015/171755 A2 | 11/2015 |

OTHER PUBLICATIONS

International Search Report and Written Opinion issued in International Patent Application No. PCT/US2022/031090, dated Sep. 20, 2022.

*Primary Examiner* — Savitha M Rao
(74) *Attorney, Agent, or Firm* — Foley & Lardner LLP

(57) ABSTRACT

Described herein are methods for decreasing triglyceride synthesis and/or decreasing triglyceride accumulation in the liver of a subject, wherein the methods comprise administering to the subject a compound of Formula (I):

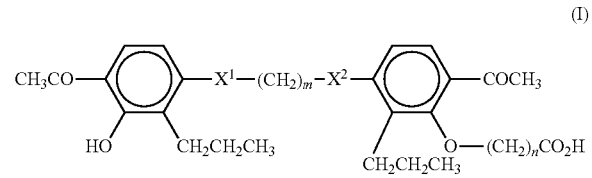

a metabolite thereof, or a pharmaceutically acceptable salt thereof.

16 Claims, 3 Drawing Sheets

(56) References Cited

U.S. PATENT DOCUMENTS

| | | |
|---|---|---|
| 7,060,854 B2 | 6/2006 | Locke et al. |
| 7,064,146 B2 | 6/2006 | Locke et al. |
| 8,835,499 B2 * | 9/2014 | Matsuda ............... C07C 59/225 514/571 |
| 9,358,217 B2 * | 6/2016 | Matsuda ................... A61P 3/06 |
| 2013/0158123 A1 | 6/2013 | Matsuda |

* cited by examiner

METHODS TO DECREASE TRIGLYCERIDE SYNTHESIS IN THE LIVER

CROSS-REFERENCE TO RELATED APPLICATIONS

This application claims the benefit of U.S. Provisional Patent Application No. 63/194,829, filed on May 28, 2021, which is incorporated herein by reference in its entirety.

FIELD

The present technology relates to decreasing triglyceride synthesis and/or reducing level of triglycerides in the liver in patients by administering phenoxyalkylcarboxylic acids such as MN-001 and MN-002.

SUMMARY

In one aspect, provided herein is a method to decrease triglyceride synthesis in a liver of a subject, the method comprising: administering to the subject an effective amount of a compound of Formula (I):

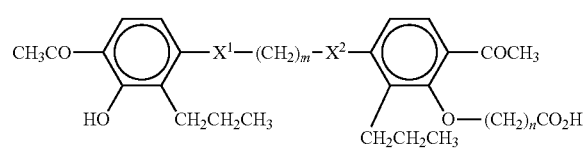

a metabolite thereof, or a pharmaceutically acceptable salt thereof, in which m is 2, 3, 4, or 5, n is 3, 4, 5, 6, 7, or 8, $X^1$ and $X^2$ each independently represent a sulfur atom, oxygen atom, sulfinyl group, or a sulfonyl group, provided that $X^1$ and $X^2$ cannot both be oxygen atoms.

In another aspect, provided herein is a method to decrease triglyceride accumulation in a liver of a subject, the method comprising: administering to the subject an effective amount of a compound of Formula (I):

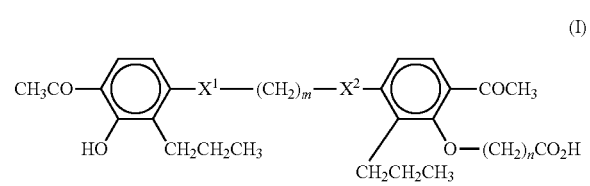

or a metabolite thereof, or a pharmaceutically acceptable salt thereof, in which m is 2, 3, 4, or 5, n is 3, 4, 5, 6, 7, or 8, $X^1$ and $X^2$ each independently represent a sulfur atom, oxygen atom, sulfinyl group, or a sulfonyl group, provided that $X^1$ and $X^2$ cannot both be oxygen atoms.

In some embodiments, the compound of Formula (I) is of Formula (IA)

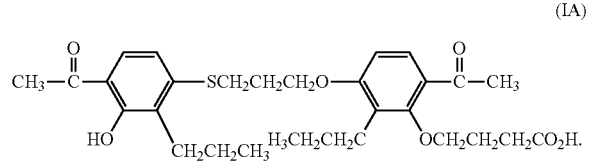

In some embodiments, the metabolite of the compound of Formula (I) is administered and is a compound of Formula (IB):

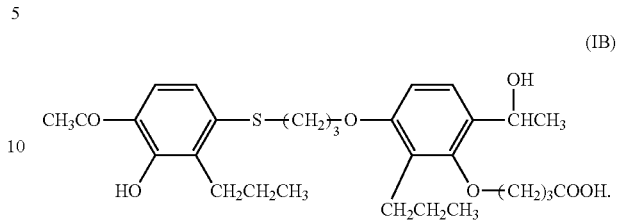

In some embodiments, the subject is diagnosed with hypertriglyceridemia, non-alcoholic fatty liver disease (NAFLD), nonalcoholic steatohepatitis (NASH), insulin resistance, pre-diabetes, or diabetes. In some embodiments, the subject is considered healthy. In some embodiments, the compound of Formula (I) is administered orally. In some embodiments, the compound of Formula (I) is administered once daily, twice daily, or thrice daily. In some embodiments, the compound of Formula (I) is administered as a liquid or solid dosage form. In some embodiments, the compound of Formula (I) is administered orally in a solid dosage form and the compound of Formula (I) is present in an orthorhombic crystalline form. In some embodiments, the compound of Formula (I) is administered in an amount ranging from 50 mg/day to 2,000 mg/day, optionally divided into one, two, or three portions. In some embodiments, the compound of Formula (I) is administered at a dosage of 50 mg, 75 mg, 100 mg, 200 mg, 500 mg, 750 mg, or 1,000 mg once a day, twice a day, or three times a day.

DETAILED DESCRIPTION

Definitions

Figure 1:
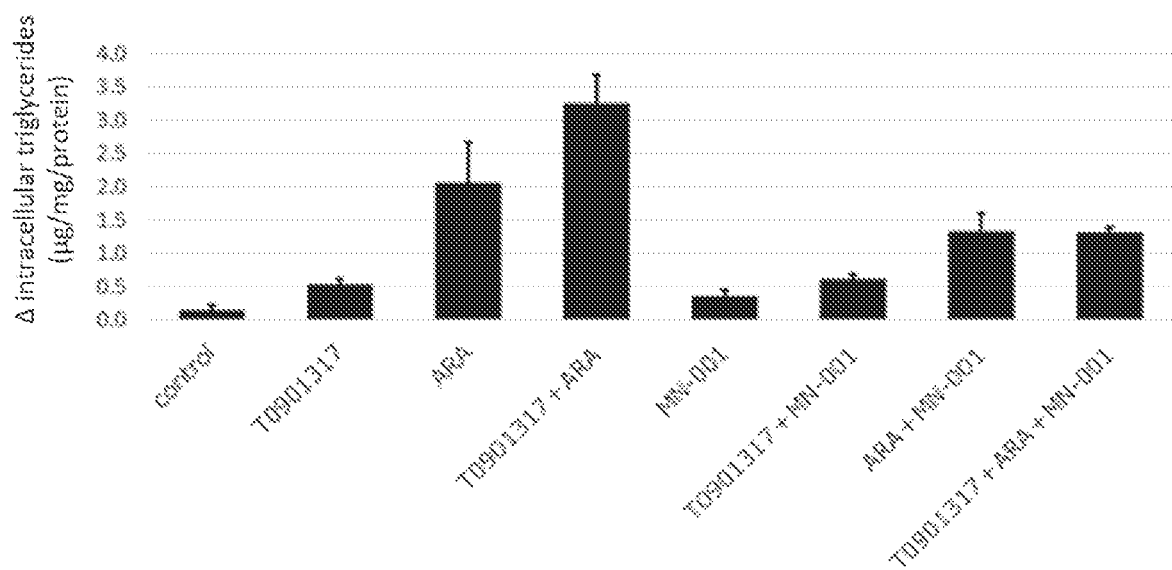
FIG. 1 depicts the measurement of intracellular triglyceride level in HepG2 cells after 48 hours incubation with one or more selected from arachidonic acid, T0901317, and MN-001. Y-axis: Δ intracellular triglycerides (μg/mg/protein).

As used herein, and in the appended claims, the singular forms "a," "an," and "the" include plural references unless the context clearly dictates otherwise.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"Cx" when placed before a group refers to the number of carbon atoms in that group to be X.

"Alkyl" refers to a monovalent acyclic hydrocarbyl radical having 1-12 carbon atoms. Non limiting examples of alkyl include methyl, ethyl, propyl, isopropyl, butyl, isobutyl, tertiary butyl, pentyl, hexyl and the like.

"Aryl" refers to a monovalent aromatic hydrocarbyl radical having up to 10 carbon atoms. Non-limiting examples of aryl include phenyl and naphthyl.

"Heteroaryl" refers to an aromatic group of from 1 to 10 carbon atoms and 1 to 4 heteroatoms selected from the group consisting of oxygen, nitrogen, sulfur within the aromatic ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Non limiting examples of heteroaryl include pyridyl, pyrrolyl, indolyl, thiophenyl, and furyl.

"Cycloalkyl" refers to a monovalent non-aromatic cyclic hydrocarbyl radical having 3-12 carbon atoms. Non limiting examples of cycloalkyl include cyclopropyl, cyclobutyl, cyclopentyl, cyclohexyl, and the like.

"Heterocyclyl" refers to a monovalent non-aromatic cyclic group of 1 to 10 carbon atoms and 1 to 4 heteroatoms selected from the group consisting of oxygen, nitrogen, sulfur within the cycle, wherein the nitrogen and/or sulfur atom(s) of the heteroaryl are optionally oxidized (e.g., N-oxide, —S(O)— or —S(O)$_2$—). Such heteroaryl groups can have a single ring (e.g., piperidinyl or tetrahydrofuranyl) or multiple condensed rings wherein the condensed rings may or may not be aromatic and/or contain a heteroatom provided that the point of attachment is through an atom of the non-aromatic heterocyclyl group. Non limiting examples of heterocyclyl include pyrrolidinyl, piperidinyl, piperazinyl, and the like.

"Amino" refers to —NH$_2$.

"Alkylamino" refers to —NHR$_B$, wherein R$_B$ is C$_1$-C$_6$ alkyl optionally substituted with 1-3 substituents independently selected from aryl, heteroaryl, cycloalkyl, and heterocyclyl group.

"Dialkylamino" refers to —N(R$_B$)$_2$, wherein Ra is defined as above.

"Comprising" shall mean that the methods and compositions include the recited elements, but not exclude others. "Consisting essentially of" when used to define methods and compositions, shall mean excluding other elements of any essential significance to the combination for the stated purpose. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

"Effective amount" of a compound utilized herein is an amount that, when administered to a patient will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Pharmaceutically acceptable" refers to non-toxic and suitable for administration to a patient, including a human patient.

"Pharmaceutically acceptable salts" refer to salts that are non-toxic and are suitable for administration to patients. Non-limiting examples include alkali metal, alkaline earth metal, and various primary, secondary, and tertiary ammonium salts. When the ester of the compound of Formula (I) includes a cationic portion, for example, when the ester includes an amino acid ester, the salts thereof can include various carboxylic acid, sulfonic acid, and mineral acid salts. Certain non-limiting examples of salts include sodium, potassium, and calcium salts.

"Protecting groups" refer to well-known functional groups which, when bound to a functional group, render the resulting protected functional group inert to the reaction to be conducted on other portions of a compound and the corresponding reaction condition, and which can be reacted to regenerate the original functionality under deprotection conditions. The protecting group is selected to be compatible with the remainder of the molecule. A "carboxylic acid protecting group" protects the carboxylic functionality of the phenoxyalkylcarboxylic acids during their synthesis. Non limiting examples of carboxylic acid protecting groups include, benzyl, p-methoxybenzyl, p-nitrobenzyl, allyl, benzhydryl, and trityl. Additional examples of carboxylic acid protecting groups are found in standard reference works such as Greene and Wuts, Protective Groups in Organic Synthesis, 2d Ed., 1991, John Wiley & Sons, and McOmie Protective Groups in Organic Chemistry, 1975, Plenum Press. Methods for protecting and deprotecting the carboxylic acids disclosed herein can be found in the art, and specifically in Greene and Wuts, supra, and the references cited therein.

"Treating" a medical condition or a patient refers to taking steps to obtain beneficial or desired results, including clinical results. For purposes of certain various aspects and certain embodiments of the present disclosure, beneficial or desired clinical results include, but are not limited to, reduction, alleviation, or amelioration of one or more manifestations of or negative effects of, or associated with, elevated levels of triglycerides in the liver, improvement in one or more clinical outcomes, diminishment of extent of disease, delay or slowing of disease progression, amelioration, palliation, or stabilization of the disease state, and other beneficial results described herein.

Triglyceride Accumulation and Triglyceride Synthesis in the Liver

The liver is the central organ for fatty acid metabolism. Fatty acids accrue in liver by hepatocellular uptake from the plasma and by de novo biosynthesis. In the setting of overnutrition and obesity, hepatic fatty acid metabolism is altered, commonly leading to the accumulation of triglycerides (TG) within hepatocytes. Long-term TG accumulation in the liver can lead to and is indicative of liver disease, such as fatty liver, NAFLD and NASH. However, TG accumulation in the liver does not necessarily correlate with elevated serum TG level and vice versa. For example, patients with early-stage hypertriglyceridemia may exhibit elevated TG level in the serum, but no TG accumulation in the liver until further disease progression. Patients suffering from a metabolic disorder such as insulin resistance, pre-diabetes, or diabetes can also demonstrate TG accumulation in the liver if the metabolic disorder is not properly treated. This liver TG accumulation can occur without elevated serum TG by de novo TG synthesis increase. Since TG accumulation in the liver is a risk factor for liver disease, there is a need for therapeutic options to prevent and/or treat TG accumulation and TG synthesis in the liver.

Methods

In one aspect, provided herein is a method to decrease triglyceride synthesis in a liver of a subject, the method comprising, consisting essentially of, or consisting of administering to the subject an effective amount of a compound of Formula (I):

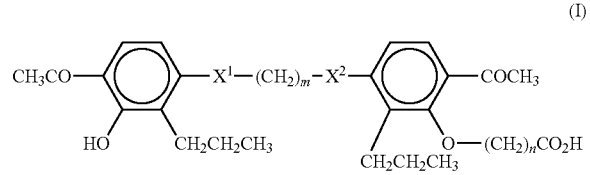

a metabolite thereof, or a pharmaceutically acceptable salt thereof, in which m is an integer from 2 to 5, n is an integer from 3 to 8, $X^1$ and $X^2$ each independently represent a sulfur atom, oxygen atom, sulfinyl group, or a sulfonyl group, provided that $X^1$ and $X^2$ cannot both be oxygen atoms.

In another aspect, provided herein is a method to decrease triglyceride accumulation in a liver of a subject, the method comprising, consisting essentially of, or consisting of administering to the subject an effective amount of a compound of Formula (I), a metabolite thereof, or a pharmaceutically acceptable salt thereof, wherein the compound of Formula (I) is defined as above.

In some embodiments, the subject is diagnosed with hypertriglyceridemia, non-alcoholic fatty liver disease (NAFLD), nonalcoholic steatohepatitis (NASH), insulin resistance, pre-diabetes, or diabetes. In some embodiments, the subject is considered healthy.

As used herein, "a metabolite thereof" refers to a metabolite that shows substantially similar therapeutic activity as a compound of Formula (I). Non limiting examples of such metabolites include compounds where the —COCH$_3$ group of a compound of Formula (I) that is attached to the phenyl containing the —O—(CH$_2$)$_n$CO$_2$H moiety is metabolized to a 1-hydroxyethyl (—CH(OH)Me) group.

Metabolites containing such a 1-hydroxyethyl group contain an asymmetric center on the 1-position of the 1-hydroxyethyl group. The corresponding enantiomers and mixtures thereof, including racemic mixtures, are included within the metabolites of the compound of Formula (I) as utilized herein.

In some embodiments, the compound of Formula (I) is a compound of Formula (IA) (or MN-001):

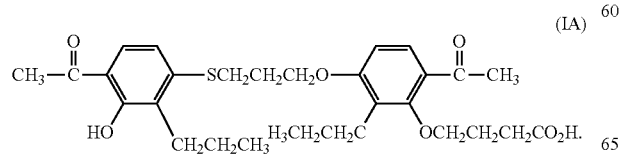

In some embodiments, the metabolite of the compound of Formula (I) and (IA) is a compound of Formula (IB) (or MN-002):

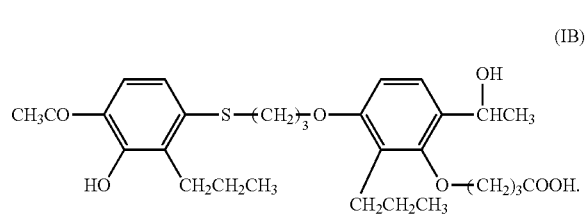

In some embodiments, the compound is administered orally. In some embodiments, the compound is administered once daily, twice daily, or thrice daily. In some embodiments, the compound is administered as a liquid or solid dosage form. In some embodiments, the compound is administered orally in a solid dosage form and is present in an orthorhombic crystalline form substantially free of other polymorphic forms.

In some embodiments, the compound is administered in an amount ranging from 50 mg/day to 5,000 mg/day, optionally divided into one, two, or three portions. In some embodiments, the compound is administered at a dosage of 25 mg, 50 mg, 75 mg, 100 mg, 150 mg, 200 mg, 250 mg, 500 mg, 750 mg, 1000 mg 1500 mg, or 2000 mg, once a day, twice a day, or three times a day. In some embodiments, the compound is administered 50 mg qd (once daily), 50 mg bid (twice daily), 50 mg tid (thrice daily), 100 mg qd, 100 mg bid, 100 mg tid, 500 mg qd, 500 mg bid, 500 mg tid, 750 mg qd, 750 mg bid, 750 mg tid, or 500 mg tid for 5 days and then 750 mg bid for another 5 days. In some embodiments, the compound is administered for at least for 1 week, 2 weeks, 3 weeks, 4 weeks, 8 weeks, 12 weeks, or indefinitely.

In some embodiments, the compound of Formula (I), the metabolite thereof, or the pharmaceutically acceptable salt thereof, is the sole active agent used in the methods disclosed herein.

Synthesis

The synthesis and certain biological activity of the compounds of Formula (I) are described in U.S. Pat. No. 4,985,585 which is incorporated herein in its entirety by reference. For example, the compound of Formula (IA) is prepared by reacting a phenol of Formula (I):

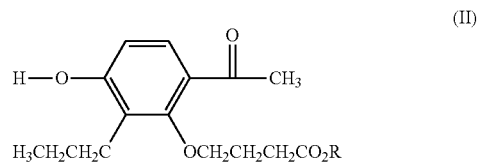

wherein, R is a carboxylic acid protecting group, with a compound of Formula (III):

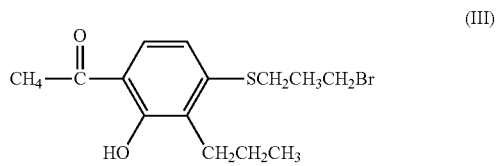

to provide a compound of Formula (IC):

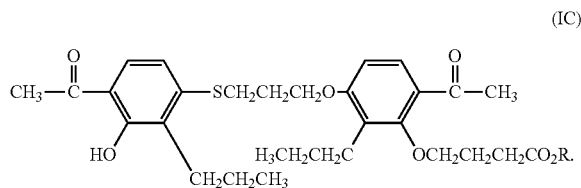

(IC)

Non limiting examples of acid protecting groups, or R groups, include $C_1$-$C_6$ alkyl, benzyl, benzhydryl, and trityl, wherein the benzyl, benzhydryl, or trityl group is optionally substituted with 1-6 $C_1$-$C_6$ alkyl, halo, and/or $C_1$-$C_6$ alkoxy groups. It will be apparent to the skilled artisan that a leaving group other than the bromo group of Formula (III) may be used. Non limiting examples of such other leaving groups include chloro or tosylate.

Deprotection of the protected carboxylic acid of Formula (IC) provides the compound of Formula (IA). As is apparent based on this disclosure, compounds of Formula (IC) are in some embodiments useful in accordance with this invention. Non-limiting examples of deprotection methods include, alkaline hydrolysis and hydrogenolysis under $H_2$ and a catalyst such as Pd/C or Pt/C.

The reactions are carried out in an inert organic solvent, for example and without limitation, acetone, methylethylketone, diethylketone, or dimethylformamide. The nucleophilic displacement reaction may be conducted at a temperature below room temperature up to the reflux temperature of the solvent, in the presence of an inorganic base, such as potassium carbonate or sodium carbonate, and optionally in the presence of potassium iodide. The reactions are carried out for a period of time sufficient to provide substantial product as determined by well-known methods such as thin layer chromatography and $^1$H-NMR. Other compounds utilized herein are made by following the procedures described herein and upon appropriate substitution of starting materials, and/or following methods well known to the skilled artisan. See also, U.S. Pat. No. 5,290,812 (incorporated herein in its entirety by reference).

The compound of Formula (IA) is recrystallized under controlled conditions to provide an essentially pure orthorhombic polymorph, referred to as Form A crystals (e.g., 90% %6 or more, preferably at least 95% Form A). Polymorphic Form A and processes for producing it are described in U.S. Pat. Nos. 7,060,854 and 7,064,146; which are incorporated herein in their entirety by reference. All polymorphic forms of the compound of Formula (I) are active, but polymorphic Form A is preferred. Under certain conditions, the solubility and the bioavailability of this polymorph is superior to the other polymorphs and thus Form A may offer improved solid formulations.

Form A crystals can be obtained, for example, by dissolving the compound of Formula (IA) in 5 to 10 parts by weight of ethanol at 25-40° C. to give a yellow to orange solution. The ethanol solution is charged with 1-10 parts of water and agitated at 20-25° C. for about 15-60 minutes and then at 5-10° C. for an additional period of 1-4 hours, preferably 2.0-3.0 hours, resulting in an off-white suspension. To this suspension is added 5-15 parts of water and the mixture is agitated at 5-10° C. for an additional 1-4 hours, preferably 1.5-2.0 hours. A solid, white to off-white product is isolated by vacuum filtration and the filter cake is washed with water and dried in a vacuum at 25-40° C. for 12-24 hours.

For compounds utilized herein that exist in enantiomeric forms, such as certain metabolites of the compound of Formula (I) (for example, the compound of formula IB), the two enantiomers can be optically resolved. Such a resolution is performed, for example, and without limitation, by forming diastereomeric salt of a base such as (S)-(−)-1-(1-naphthyl) ethylamine with the corresponding carboxylic acid compound, or by separating the enantiomers using chiral column chromatography. Intermediates to such compounds, which intermediates also exist in enantiomeric forms can be similarly resolved.

Administration and Formulation

The compounds utilized herein can be administered orally, or by intravenous, intramuscular, and subcutaneous injection, or transdermal methods. Effective dosage levels can vary widely, e.g., from about 100 to 4000 mg per day. In some embodiments, the daily dosage range is 250 to 2,000 mg, given in one, two or three portions. In some embodiments, the dosage is 1000 mg twice a day. In some embodiments, suitable dosages include 1000 mg qd, 1000 mg bid, and 750 mg tid.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Therapeutic compositions containing the compounds utilized herein will ordinarily be formulated with one or more pharmaceutically acceptable ingredients in accordance with known and established practice. In general, tablets are formed utilizing a carrier such as modified starch, alone or in combination with 10% by weight of carboxymethyl cellulose (Avicel). The formulations are compressed at from 1,000 to 3,000 pounds pressure in the tablet forming process. The tablets preferably exhibit an average hardness of about 1.5 to 8.0 kp/cm², preferably 5.0 to 7.5 kp/cm². Disintegration time varies from about 30 seconds to about 15 or 20 minutes.

Formulations for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compounds utilized herein can be formulated as aqueous suspensions in admixture with pharmaceutically acceptable excipients such as suspending agents, e.g., sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monooleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or -n-propyl-p-hydroxy benzoate, one or more coloring agents, one or more flavoring agents and one or more sweetening agents, such as glycerol, sorbitol, sucrose, saccharin or sodium or calcium cyclamate.

Suitable formulations also include sustained release dosage forms, such as those described in U.S. Pat. Nos. 4,788,055; 4,816,264; 4,828,836; 4,834,965; 4,834,985; 4,996,047; 5,071,646; and, 5,133,974, the contents of which are incorporated herein in their entirety by reference.

Other forms suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compounds utilized herein may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds utilized herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds utilized herein may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds utilized herein may be formulated for vaginal administration. Pessaries, tampons, creams, gels, pastes, foams or sprays containing in addition to the active ingredient such carriers as are known in the art to be appropriate.

The compounds utilized herein may be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compounds utilized herein may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

When desired, formulations can be prepared with enteric coatings adapted for sustained or controlled release administration of the active ingredient. A common type of controlled release formulation that may be used for the purposes of the present invention comprises an inert core, such as a sugar sphere, a first layer, coated with an inner drug-containing second layer, and an outer membrane or third layer controlling drug release from the inner layer.

The cores may be of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (EUDRAGIT® NE-30-D) and ammonio methacrylate copolymer types A and B (EUDRAGIT® RL30D and RS30D), and silicone elastomers. Usually, a plasticizer is used together with the polymer. Exemplary plasticizers include:

dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the formulations. In such forms, the formulation is subdivided into unit dosages containing appropriate quantities of the active component (e.g., and without limitation, a compound of Formula (I) a metabolite thereof, or a pharmaceutically acceptable salt thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

EXAMPLES

Example 1

HepG2 cells (derived from human hepatocellular carcinoma samples) were incubated with one or more selected from 10 µM arachidonic acid (ARA), 1 µM LXR agonist T0901317 ("T1317"), and 10 µM MN-001 for 48 hours.

T1317 stimulates LXR-SREBP-1c ChREPB signal, increases triglyceride (TG) synthesis in liver and exacerbates fatty liver. The intracellular triglyceride level was measured after the treatment (FIG. 1).

Compared to vehicle, T1317 increased TG synthesis by 3.8-fold; ARA increased TG synthesis by 15.3-fold; and the combination of T1317 and ARA increased TG synthesis by 24.3-fold.

Adding MN-001 inhibited TG accumulation (TG synthesis) caused by ARA and/or T1317 in HepG2 cells. More particularly, the addition of MN-001 suppressed the increase by 1.7-fold in TG synthesis by T1317, by 3.7-fold in TG synthesis by ARA or by a combination of T1317 and ARA. These results may be related to the suppression of TG reduction and fatty liver formation by suppressing VLDL secretion.

The effect of MN-001 on the mRNA expression of molecules related to TG metabolism: (1) fatty acid translocase/CD36, which is involved in the uptake of ARA into hepatocytes in the liver, and (2) ABCG1, which plays a role in controlling tissue lipid levels by mediating transfer of cellular cholesterol to HDL, were also investigated by measuring extracted RNA from HepG2 cells and using real-time PCR. To this end, RNA was extracted from HepG2 cells (after treatment with one or more selected from 10 µM arachidonic acid (ARA), 1 µM T1317, and 10 µM MN-001 for 48 hours) and converted to cDNA.

Figure 2:
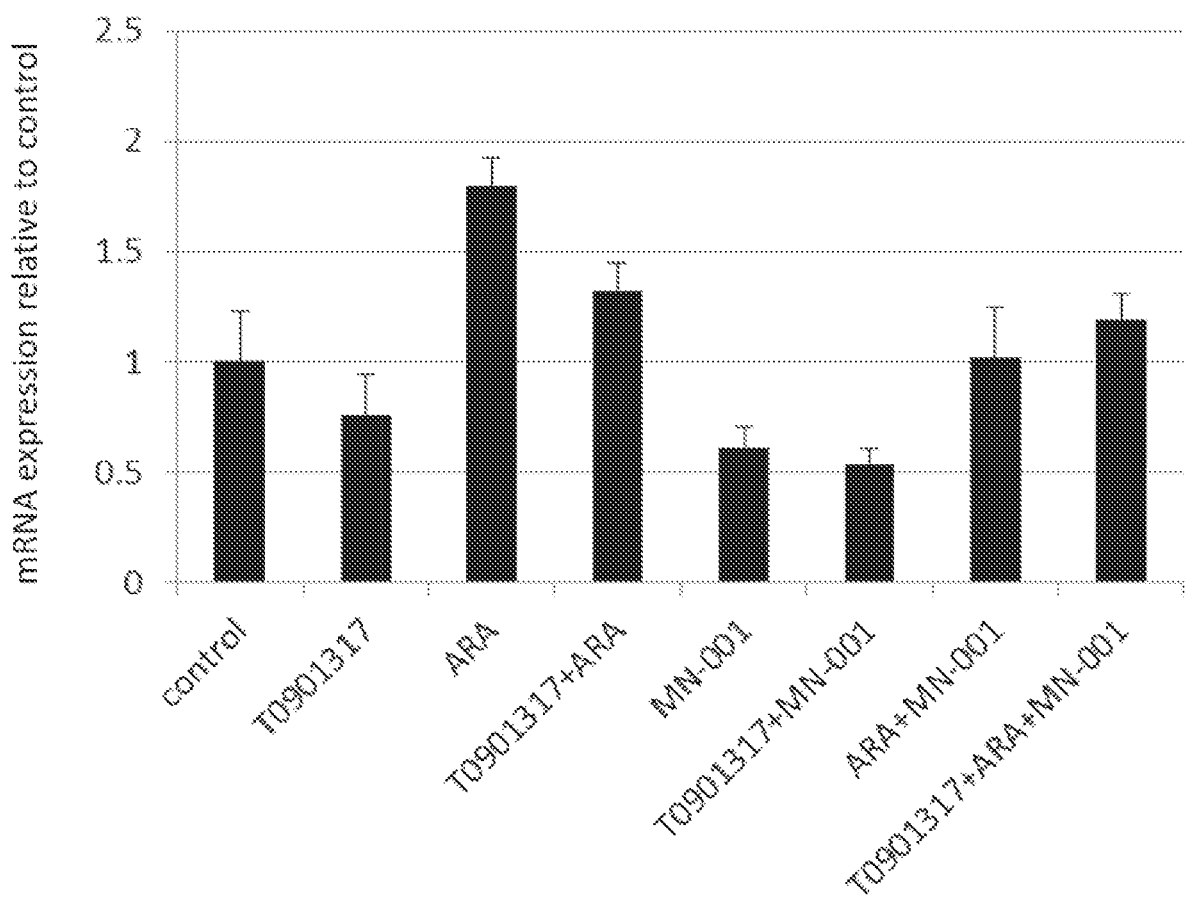
FIG. 2 depicts the measurement of CD36 mRNA expression levels from HepG2 cells after treatment with one or more selected from arachidonic acid, T0901317, and MN-001. Y-axis: relative mRNA expression (arbitrary units) compared to a control.

After conversion to cDNA, the CD36 mRNA expression levels were measured by qPCR (FIG. 2). Free fatty acids are taken up into cells via a receptor complex containing CD36, which is upregulated in insulin-resistant states. Saturated fatty acids (e.g., palmitic acid, stearic acid) and fructose induce adipogenic pathways and promote fat accumulation by increasing CD36 expression and modulating ChREBP, which regulates lipogenesis. In this experiment, ARA increased CD36 expression by 1.8 fold compared to control, MN-001 downregulated CD36 expression by 0.6 fold compared to control and adding MN-001 to ARA suppressed CD36 expression by 0.6 fold compared to ARA alone. More particularly, treatment with MN-001 lowered CD36 expression by 39% and 43% in the absence and presence of ARA, respectively, thereby indicating that MN-001 inhibited cellular update of ARA.

Figure 3:
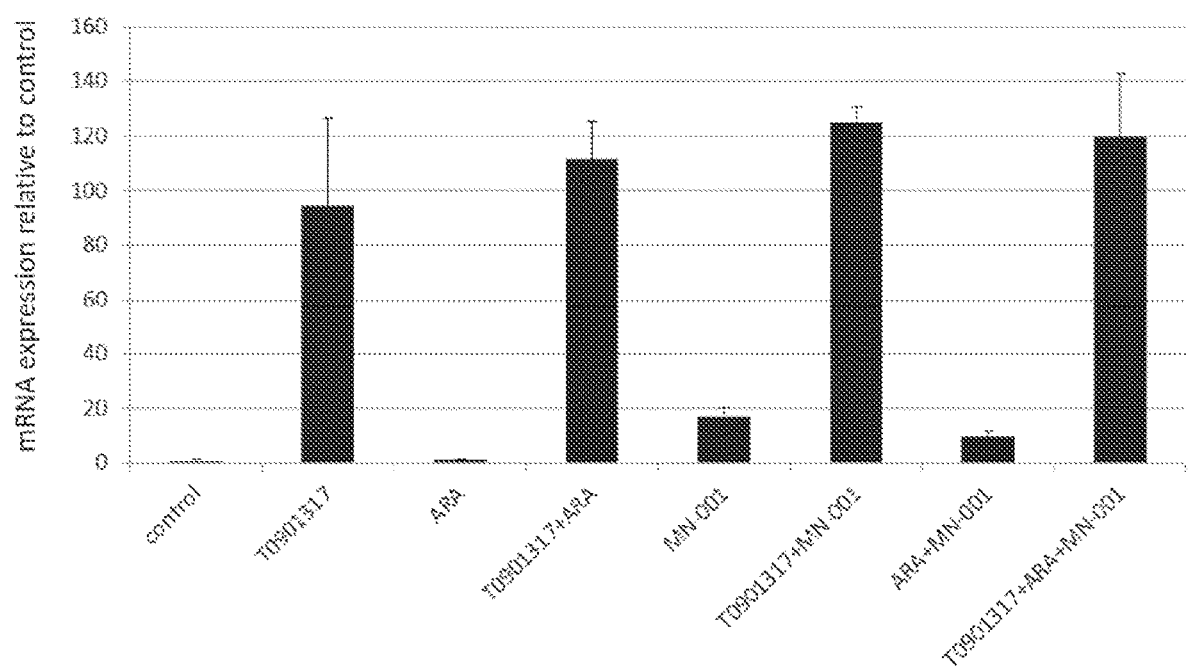
FIG. 3 depicts the measurement of ABCG1 mRNA expression levels from HepG2 cells after treatment with one or more selected from arachidonic acid, T0901317, and MN-001. Y-axis: relative mRNA expression (arbitrary units) compared to a control.

In addition, the ABCG1 mRNA expression levels were also measured by qPCR (FIG. 3). ABCG1 is known to be highly expressed in lipid-loaded macrophages and mediates cholesterol efflux to HDL. ABCG1 deficiency leads to profound intracellular cholesterol accumulation in macrophages and hepatocytes. In this experiment, MN-001 upregulated ABCG1 expression by 17-fold compared to control, whereas ARA+MN-001 upregulated ABCG1 expression by 9.7-fold compared to control.

Example 2

A Phase 2 multi-center, double-blind, randomized, placebo-controlled study is conducted to evaluate the efficacy, safety, and tolerability of MN-001. Patients with non-alcoholic fatty liver disease (NAFLD), Type 2 diabetes mellitus (DM), and hypertriglyceridemia are informed and asked to participate in the study. The study consists of a Screening Phase (up to −8 weeks) followed by a Treatment Phase (24 weeks), and a Follow-up visit (approximately one week after the last dose).

The sample population for this trial includes male and female participants ≥21 and 575 years of age with diagnosis of NAFLD confirmed by MRI scan (MRI-PDFF >8%), Type 2 diabetes and hypertriglyceridemia.

The co-primary objectives of the study are:

Change in liver fat content measured by MRI Proton Density Fat Fraction (MRT-PDFF) at Week 24

Change from baseline in fasting serum triglyceride levels at Week 24

The secondary objectives are:

To evaluate the safety and tolerability of MN-001

To evaluate the effect of MN-001 on lipid profile

HDL-C, LDL-C, total cholesterol level

Screening Phase (Up to 8 Weeks)

A total of up to 8 weeks are allotted to complete the screening assessments. During the Screening Phase, participants will be assessed for study eligibility. The following assessments are performed: MRI-PDFF (magnetic resonance imaging proton density fat fraction), medical history including review of current and prior medications, abbreviated physical examination including height and body weight, vital signs and 12-ECG. Blood samples are obtained for complete blood count (CBC), complete metabolic panel (CMP), fasting lipid panel, and coagulation panel (PT/INR). Urinalysis is performed, and for pre-menopausal female participants, a serum human chorionic gonadotrophin (β-hCG) pregnancy test is given.

Treatment Phase (24 Weeks)

MN-001 250 mg tablet PO bid or matching placebo is administered bid for 24 weeks. Throughout the Double-blind Treatment (DBT) Phase, safety parameters are assessed, and concomitant medications are documented.

End of Study Visit

All patients who complete the study return for a follow up visit approximately one week (±3 days) after end of treatment. Vital signs, body weight, blood sample collected for clinical safety labs, and concomitant medications (CMs) and adverse events (AEs) are documented.

Certain Embodiments

Embodiment 1. A method to decrease triglyceride synthesis in a liver of a subject, the method comprising: administering to the subject an effective amount of a compound of Formula (I):

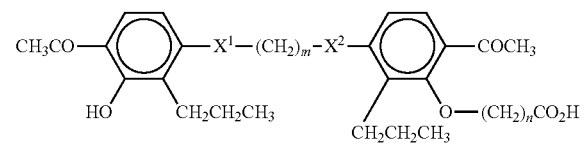

(I)

a metabolite thereof, or a pharmaceutically acceptable salt thereof, in which m is 2, 3, 4, or 5, n is 3, 4, 5, 6, 7, or 8, and $X^1$ and $X^2$ each independently represent a sulfur atom, oxygen atom, sulfinyl group, or a sulfonyl group, provided that $X^1$ and $X^2$ cannot both be oxygen atoms.

Embodiment 2. The method of Embodiment 1, in which the compound of Formula (I) is of Formula (IA)

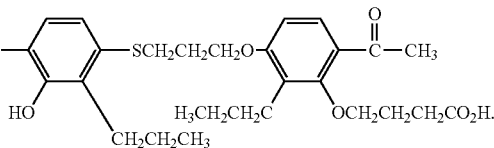

(IA)

Embodiment 3. The method of Embodiment 1, in which the metabolite of the compound of Formula (I) is administered and is a compound of Formula (IB):

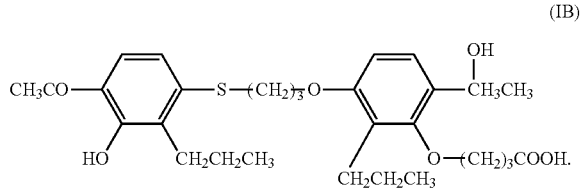

(IB)

Embodiment 4. The method of any one of Embodiments 1-3, wherein the subject is diagnosed with hypertriglyceridemia, non-alcoholic fatty liver disease (NAFLD), nonalcoholic steatohepatitis (NASH), insulin resistance, pre-diabetes, or diabetes.

Embodiment 5. The method of any one of Embodiments 1-3, wherein the subject is considered healthy.

Embodiment 6. The method of any one of Embodiments 1-5, wherein the compound of Formula (I) is administered orally.

Embodiment 7. The method of any one of Embodiments 1-6, wherein the compound of Formula (I) is administered once daily, twice daily, or thrice daily.

Embodiment 8. The method of any one of Embodiments 1-7, wherein the compound of Formula (I) is administered as a liquid or solid dosage form.

Embodiment 9. The method of any one of Embodiments 1-8, wherein the compound of Formula (I) is administered orally in a solid dosage form and the compound of Formula (I) is present in an orthorhombic crystalline form.

Embodiment 10. The method of any one of Embodiments 1-9, wherein the compound of Formula (I) is administered in an amount ranging from 50 mg/day to 2,000 mg/day, optionally divided into one, two, or three portions.

Embodiment 11. The method of any one of Embodiments 1-10, wherein the compound of Formula (I) is administered at a dosage of 50 mg, 75 mg, 100 mg, 200 mg, 500 mg, 750 mg, or 1,000 mg once a day, twice a day, or three times a day.

Embodiment 12. A method to decrease triglyceride accumulation in a liver of a subject, the method comprising: administering to the subject an effective amount of a compound of Formula (I):

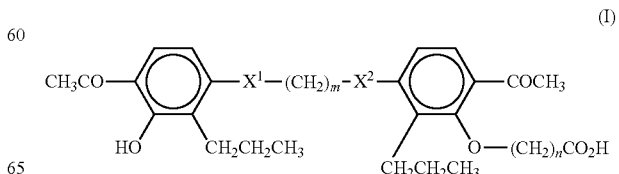

(I)

or a metabolite thereof, or a pharmaceutically acceptable salt thereof, in which m is 2, 3, 4, or 5, n is 3, 4, 5, 6, 7, or 8, $X^1$ and $X^2$ each independently represent a sulfur atom, oxygen atom, sulfinyl group, or a sulfonyl group, provided that $X^1$ and $X^2$ cannot both be oxygen atoms.

Embodiment 13. The method of Embodiment 12, wherein the compound of Formula (I) is of Formula (IA)

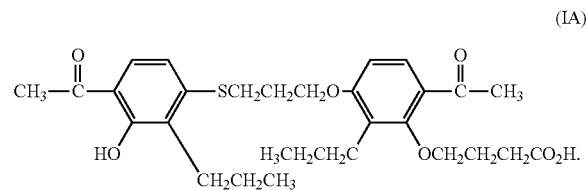

(IA)

Embodiment 14. The method of Embodiment 12, wherein the metabolite of the compound of Formula (I) is a compound of Formula (IB):

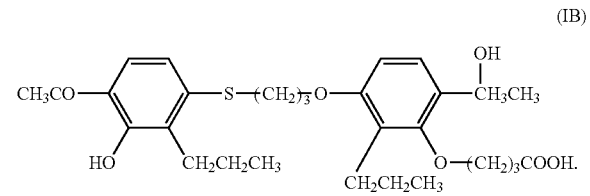

(IB)

Embodiment 15. The method of any one of Embodiments 12-14, wherein the subject is diagnosed with hypertriglyceridemia, non-alcoholic fatty liver disease (NAFLD), non-alcoholic steatohepatitis (NASH), insulin resistance, pre-diabetes, or diabetes.

Embodiment 16. The method of any one of Embodiments 12-14, wherein the subject is considered healthy.

Embodiment 17. The method of any one of Embodiments 12-16, wherein the compound of Formula (I) is administered orally.

Embodiment 18. The method of any one of Embodiments 12-17, wherein the compound of Formula (I) is administered once daily, twice daily, or thrice daily.

Embodiment 19. The method of any one of Embodiments 12-18, wherein the compound of Formula (I) is administered as a liquid or solid dosage form.

Embodiment 20. The method of any one of Embodiments 12-19, wherein the compound of Formula (I) is administered orally in a solid dosage form and the compound of Formula (I) is present in an orthorhombic crystalline form.

Embodiment 21. The method of any one of Embodiments 12-20, wherein the compound of Formula (I) is administered in an amount ranging from 50 mg/day to 2,000 mg/day, optionally divided into one, two, or three portions.

Embodiment 22. The method of any one of Embodiments 12-21, wherein the compound of Formula (I) is administered at a dosage of 50 mg, 75 mg, 100 mg, 200 mg, 500 mg, 750 mg, or 1,000 mg once a day, twice a day, or three times a day.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method to decrease triglyceride synthesis in a liver of a subject, the method comprising: administering to the subject an effective amount of a compound of Formula (I):

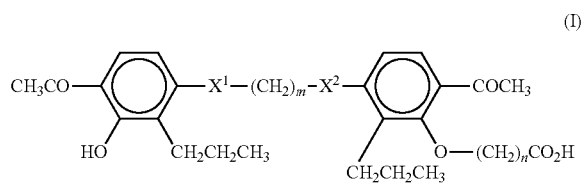
(I)

a metabolite thereof, or a pharmaceutically acceptable salt thereof, in which m is 2, 3, 4, or 5, n is 3, 4, 5, 6, 7, or 8, and $X^1$ and $X^2$ each independently represent a sulfur atom, oxygen atom, sulfinyl group, or a sulfonyl group, provided that $X^1$ and $X^2$ cannot both be oxygen atoms, wherein the subject is diagnosed with insulin resistance, pre-diabetes, or diabetes.

2. The method of claim 1, in which the compound of Formula (I) is of Formula (IA)

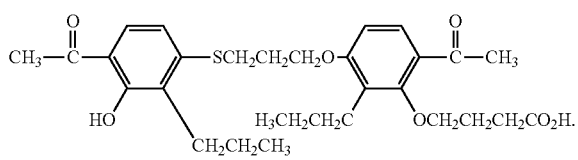
(IA)

3. The method of claim 1, in which the metabolite of the compound of Formula (I) is administered and is a compound of Formula (IB):

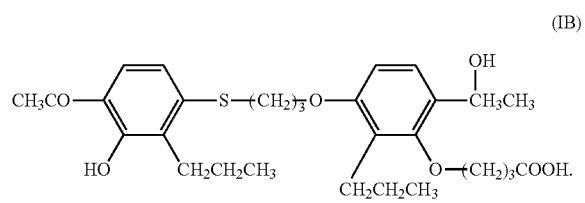
(IB)

4. The method of claim 1, wherein the compound of Formula (I) is administered orally.

5. The method of claim 1, wherein the compound of Formula (I) is administered once daily, twice daily, or thrice daily.

6. The method of claim 1, wherein the compound of Formula (I) is administered as a liquid or solid dosage form.

7. The method of claim 1, wherein the compound of Formula (I) is administered orally in a solid dosage form and the compound of Formula (I) is present in an orthorhombic crystalline form.

8. The method of claim 1, wherein the compound of Formula (I) is administered in an amount ranging from 50 mg/day to 2,000 mg/day, optionally divided into one, two, or three portions.

9. A method to decrease triglyceride accumulation in a liver of a subject, the method comprising: administering to the subject an effective amount of a compound of Formula (I):

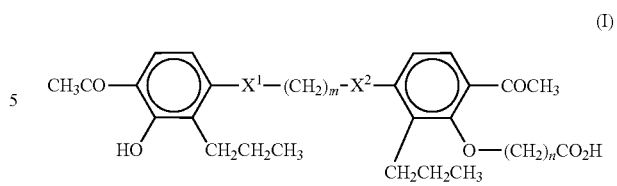
(I)

or a metabolite thereof, or a pharmaceutically acceptable salt thereof, in which m is 2, 3, 4, or 5, n is 3, 4, 5, 6, 7, or 8, $X^1$ and $X^2$ each independently represent a sulfur atom, oxygen atom, sulfinyl group, or a sulfonyl group, provided that $X^1$ and $X^2$ cannot both be oxygen atoms, wherein the subject is diagnosed with insulin resistance, pre-diabetes, or diabetes.

10. The method of claim 9, wherein the compound of Formula (I) is of Formula (IA)

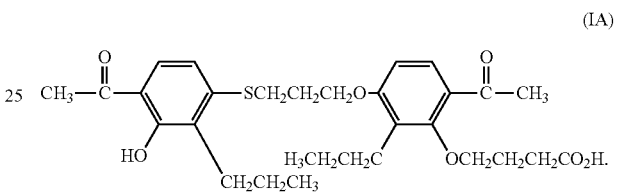
(IA)

11. The method of claim 9, wherein the metabolite of the compound of Formula (I) is a compound of Formula (IB):

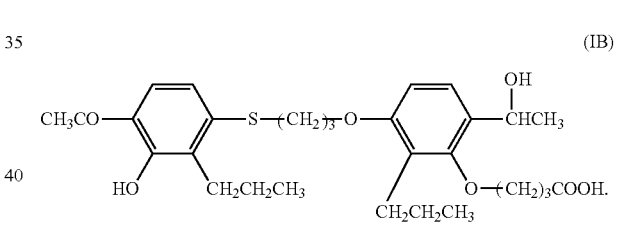
(IB)

12. The method of claim 9, wherein the compound of Formula (I) is administered orally.

13. The method of claim 9, wherein the compound of Formula (I) is administered once daily, twice daily, or thrice daily.

14. The method of claim 9, wherein the compound of Formula (I) is administered as a liquid or solid dosage form.

15. The method of claim 9, wherein the compound of Formula (I) is administered orally in a solid dosage form and the compound of Formula (I) is present in an orthorhombic crystalline form.

16. The method of claim 9, wherein the compound of Formula (I) is administered in an amount ranging from 50 mg/day to 2,000 mg/day, optionally divided into one, two, or three portions.

* * * * *